United States Patent [19]

Roberts

[11] Patent Number: 4,806,537
[45] Date of Patent: Feb. 21, 1989

[54] USE OF AMODIAQUIN AND RELATED COMPOUNDS IN TREATMENT OF NERVOUS SYSTEM DEGENERATION

[75] Inventor: Eugene Roberts, Monrovia, Calif.

[73] Assignee: City of Hope, Duarte, Calif.

[21] Appl. No.: 171,371

[22] Filed: Mar. 21, 1988

Related U.S. Application Data

[63] Continuation-in-part of Ser. No. 39,017, Apr. 16, 1987, abandoned, which is a continuation of Ser. No. 946,068, Dec. 24, 1986, abandoned.

[51] Int. Cl.⁴ .................... A61K 31/50; A61K 31/495
[52] U.S. Cl. .................................................. 514/253
[58] Field of Search ......................................... 514/253

[56] References Cited

U.S. PATENT DOCUMENTS 4,140,775  2/1979  McCall ............................... 514/253

Primary Examiner—Stanley J. Friedman
Attorney, Agent, or Firm—Edward S. Irons

[57] ABSTRACT

A procedure for the treatment of degenerative diseases of the central nervous system, including Alzeheimer's disease, multiple sclerosis and the like, by the administration of amodiaquin and related compounds is disclosed.

10 Claims, No Drawings

USE OF AMODIAQUIN AND RELATED COMPOUNDS IN TREATMENT OF NERVOUS SYSTEM DEGENERATION

This application is a continuation-in-part of application Ser. No. 039,017 filed Apr. 16, 1987, which in turn is a continuation-in-part of Ser. No. 946,068 filed Dec. 24, 1986 (both are now abandoned).

BACKGROUND OF THE INVENTION

This invention comprises a method for treatment of degenerative diseases of the human central nervous system (CNS), including senile dementia of the Alzheimer's type, multiple sclerosis, and amyotrophic lateral sclerosis (hereinafter referred to as AD, MS and ALS, respectively) and related conditions.

ALZHEIMER'S DISEASE (AD)

AD is a progressive degenerative disorder of the CNS leading to severe disturbances in perception, memory, and overall neurological function. In advanced cases, gross pathological alterations are visible in structures of the brain. A large body of current research is directed to elucidating the causes and mechanisms of this disease and to halting or reversing its debilitating and eventually fatal progress. Such research indicates that symptoms of AD reflect the inability of the organism to continue to compensate for continuing degenerative changes in the biochemical machinery of cells of the brain.

Ideally, a living organism and its parts are cybernetic: the various elements effectively communicate with and respond to each other and to the environment in an adaptive way to maintain an ideal, steady-state condition. In AD, whether one looks at neuropathologic, physiologic, neurochemical or behavioral aspects, a final common path is taken by organisms when behavioral options ordinarily available to achieve adaptive responses are precluded by degeneration of the neural machinery. Early degenerative changes are compensated for by activities of redundant neuralelements and by adjustments in neural feedback and modular systems. However, eventually pathologic changes may become sufficiently extensive so that the latter activities are inadequate and social behavior and physiological responses of a severely affected individual become maladaptive. Survival then becomes dependent upon extensive use of artificial social and medical support systems. The end-stage pathologies observed at autopsy are characterized by a variety of degenerative changes in cells in many brain regions. There are losses of neuronal cells, decreases in neuronal processes in surviving cells, and increases in glial cellular elements.

Accelerated degeneration of neural, endothelial, neuroendrocrine, and endocrine elements, together with incoordination in the networks of relations among the cellular components of the immune system and coincident disruption of neurovascular relations and breakdown of the blood brain barrier in the affected regions, predisposes to the development of both circulating and cellular autoantibodies to various cellular and extracellular components in the disrupted regions. This leads to enhanced cellular destruction and deposition of indigestible debris of immune complexes in capillaries and extracellular sites. A consequence of perturbation of the immune system is immunosuppression with resultant activation of latent viruses destructive to the nervous system.

Because AD of the sporadic type almost always occurs coextensively with aging, some pathological features are shared. However, AD should not be considered in the same category as normal attritional types of aging because, in addition to general types of aging changes, important pathological differences are noted in brain tissue and genetic components exist in familial AD. There are pedigrees showing what appears to be an autosomal dominant transmission of the disorder. Idiosyncratic reactions to ubiquitously present environmental factors may play an important role in the development of AD.

In AD, the degenerative changes observed in several brain regions are correlated with initial malfunction and subsequent degeneration of terminals of neurons whose cell bodies lie in regions of the brain stem core and whose fibers project to many structures both above and below their location. In AD, there often is a specific and critical loss of cholinergic neurons in the basal nucleus of Meynert[1] and sometimes of the noradrenergic neurons in the locus ceruleus.[2] The latter regions are the major sources of cholinergic and noradrenergic neurons of the CNS, respectively, projecting widely and diffusely upon all telencephalic structures. There is evidence that the hippocampus, a region of the brain known to play a key role in memory formation, essentially may be removed from brain circuitry by lesions at its input and output sites.[3]

[1] See, Whitehouse, P. J., Price, D. L., Clark, A. W., Coyle, J. T., and DeLong, M. R., *Ann. Neurol.*, 10. 122–126 (1981).
[2] See, Bondareff, W., Mountjoy, C. Q. and Roth, M., *Neurology*, 32, 164–168 (1982).
See, Hyman, B. T., Van Hoesen, G. W., Damasio, A. R. and Barnes, C. L., *Science*, 225, 1168–1170 (1984).

Many therapeutic efforts have been aimed at attempting to enhance cholinergic function, the decrement of which is believed to underlie much of the cognitive disorder of AD. The best of these have had small and only evanescent ameliorative effects. However, one approach that remains to be refined is the introduction of an effective inhibitor of acetylcholine breakdown (acetylcholinesterase inhibitor) that would remain at critical sites of neurotransmission for long periods of time.

MULTIPLE SCLEROSIS (MS)

Multiple sclerosis (MS) is the most common degenerative, inflammatory neurological disease which affects people earlier than AD does (at 20 to 40 years of age). In MS, the insulating nerve covering (myelin) is disrupted in the central nervous system (brain and spinal cord). When myelin is damaged or destroyed (demyelination), nerve impulses are short-circuited, and there is a slowing or blocking of transmission along nerve fibers.

In MS, mild and severe, a variety of symptoms occur such as impaired vision, numbness, muscle weakness and fatigue. There is a waxing and waning of symptoms; unpredictable improvements and exacerbations occur. However, there is an inevitable downhill course, all patients eventually becoming progressively debilitated and dying from the disease. Effective treatments are being sought, but to date none has been found. Many of the overt symptoms are believed to be related to inadequate cholinergic function.

MS is an autoimmune disease, in which for unknown reasons cells of the immune system attack the myelin surrounding the nerve fibers, as a result of which inflammation occurs. Control of MS symptoms must be based on developing methods of regulating immune system function.

Therapies and treatments currently being tested include antiviral and anti-inflammatory agents (Prednisone, methylprednisone, adrenocorticotropic hormone (ACTH), immunosuppressants (cyclosporine, azathioprine, and total lymphoid irradiation), and immunomodulators (the interferons and co-polymer I). To date, none of the above has been shown to be significantly effective.

AMYOTROPHIC LATERAL SCLEROSIS (ALS)

ALS is a progressive disease which proceeds at variable rates to death in months or years. It is characterized by insidious onset of motor weakness, clumsiness and muscle wasting. As in AD and MS, cholinergic function may be involved to some extent. Pathologically, there is a degeneration of the ganglion cells of the anterior horns in the spinal cord. There is deposition of lipochrome, perivascular infiltration of round cells. Large axonal swellings are found containing large numbers of neurofilaments. There is degeneration of the white matter of the spinal cord, of ganglion cells of the medullary motor nuclei, and of the motor and premotor cortex. Many ALS patients are sensitive to the slightest changes in temperature. Elevated temperatures worsen symptoms, while a decrease improves them.

ALS is a progressive, uniformly fatal disease that may run a 1-5 year course, rarely as long as 15 years. It is a disease of late middle life and occurs worldwide. The cause is at present unknown, but cases of dominant, recessive and X-linked hereditary have been described. There is some suggestive evidence of a viral etiology, since a few cases have occurred following *enceohalitis letharoica*. However, truly convincing evidence of viral transmission is lacking. Injury to the anterior horn cells of the spinal cord, by whatever mechanism, may be a predisposing factor, resulting in the occurrence of a premature aging process. Thyrotropin releasing hormone (TRH), transfer factor, guanidine, and many other substances have been found to be therapeutically ineffective in ALS.

SUMMARY OF THE INVENTION

This invention entails the therapeutic use of the substance, amodiaquin, that embodies in a single molecular structure[4] the Properties required to treat AD, MS and ALS and related disorders. Administration of amodiaquin in an effective amount blocks the $K^+$ channels, decreases the rate of breakdown in the neurotransmitter acetylcholine, thus enhancing nerve function, and decreases undesirable autoimmune reactions of immune lymphocytes.

[4] The molecular structure of amodiaquin is set forth at page 77 (Compound No. 606) of The Merck Index, Ninth Edition (1976).

The invention also entails a like therapeutic use of certain structural variants of amodiaquin and of amodiaquin metabolites including desethylamodiaquine, bisdesethylamodiaquine and 2-hydroxydesethylamodiaquine.[5]

[5] Such amodiaquin metabolites are described in Mount, et al., "Sensitive Analysis of Blood for Amodiaquine and Three Metabolites by High-Performance Liquid Chromatography with Electrochemical Detection," *Journal of Chromatography, Biomedical Applications*, 383, 375-386 (1986).

DETAILED DESCRIPTION OF THE INVENTION

Amodiaquin is an effective cholinesterase inhibitor.[6] However, its ability to block $K^+$ channels has not previously been reported. Whereas therapies might theoretically be devised in which substances that are cholinesterase inhibitors and others that are $K^+$ channel blockers might be administered to patients simultaneously, it is impossible that together such substances could penetrate equally well to the same nervous system sites at the same time and would accumulate in nervous system structures in appropriate concentrations. This invention entails the therapeutic use of a single substance, amodiaquin, to perform the required therapeutic functions at the same sites at the same time.

[6] See, Go, M. L., Ngiam, T. L. and Wan, A. S. C., *Southeast Asian J. Trop. Med. Public Heath*, 12(1), 37-41 (1981).

There already exists a large literature dealing with a $K^+$ channel blocker, 4-aminopyridine (4AP),[7] the administration of which rapidly overcomes the effects of general anesthesia[8] and which may improve symptoms in some patients with AD.[9] 4AP may be prototypic of a class of drugs that block voltage-gated $K^+$ channels in cells in many regions of the body, from brain to lymphocyte.

[7] See, Soni, N. and Kam, P., *Anaesthesia and Intensive Care*, 10, 120-126 (1982).
[8] Booth, N. H., Hatch, R. C. and Crawford, L. M., *American Journal of Veterinary Research*, 43, 1227-1231 (1982); Hatch, R. C., Booth, N. H., Kitzman, J. V., Wallner, B. M. and Clark, J. D., *American Journal of Veterinary Research*, 44, 417-423 (1983); Martinez-Aguirre, E. and Crul, J. F., *Acta Anaesthesiologica Belgica*, 30, 231-238 (1979); and Wallner, B. M., Hatch, R. C., Booth, N. H., Kitzman, J. V., Clark, J. D. and Brown, J., *American Journal of Veterinary Research*, 43, 2259-2265 (1982).
[9] See, Wesseling, H., Agoston, S., Van Dam, G. B. P., Pasma, J., DeWitt, D. J. and Havinga, H., *New England Journal of Medicine*, 310, 988-999 (1984).

Results from experiments ranging from those with intact animals to isolated nerve terminals and from receptors to the cortex and thence to the neuromuscular junction are consistent with the interpretation that 4AP can enhance the release of all neurotransmitters and neuromodulators as a result of blocking $K^+$ channels at all levels of the CNS.[10] 4AP partially reversed the behavioral deficit produced by anoxia in mice.[11]

[10] See, Agoston, D., Hargittai, P. and Nagy, A., *Journal of Neurochemistry*, 41, 745-751 (1983); Buckle, P. J. and Haas, H. L., *Journal of Physiology*, 326, 109-122 (1982); Casamenti, F., Corradetti, R., Loffelhoz, K., Mantovani, P. and Pepeu, G., *British Journal of Pharmacology*, 76, 439-445 (1982); Dolezal, V. and Tucek, S., *Naunyn-Schmiedeberos Archives of Pharmacology*, 323, 90-95 (1983); Jankowska, E., Lundberg, A., Rudomin, P. and Sykova, E., *Brain Research*, 240, 117-129 (1982); Laskey, W., Schondorf, R. and Polosa, C., *Journal of the Autonomic Nervous System*, 11, 201-206 (1984); Murray, N. M. F. and Newsom-Davis, J., *Neurology*, 31, 265-271 (1981); Tapia, R. and Sitges, M., *Brain Research*, 250, 291-299 (1982); and Thomsen, R. H. and Wilson, D. F., *Journal of Pharmacology and Experimental Therapeutics*, 227, 260-265 (1983).
[11] Gibson, G. E., Pelmas, C. J. and Peterson, C., *Pharmacology, Biochemistry and Behavior*, 18, 909-916 (1983).

After stimulation of lymphocytes by phytohemagglutinin, there is stimulation of the uptake of $K^+$, and recently it has been demonstrated that voltage-gated $K^+$ channels must be opened in the presence of phytohemagglutinins or alloantigens.[12] Metabolic events consequent to activation, such as DNA and protein synthesis, including interleukin-2 production, are inhibited by $K^+$ channel blockers.[13]

[12] See, Cahalan, M. D., Chandy, K. G., deCoursey, T. E. and Gupta, S., *Journal of Physiology*, 358, 197-237 (1985); and Chandy, K. G., deCoursey, T. E., Cahalan, M. D., McLaughlin, C. and Gupta, S., *Journal of Experimental Medicine*, 160, 369∝385 (1984).
[13] See, Chandy, K. G., deCoursey, T. E., Cahalan, M. D., McLaughlin, C. and Gupta, S., *Journal of Experimental Medicine*, 160, 369-385 (1984).

This invention implicates a realization that substances effective to block voltage-gated $K^+$ channels may heighten potentialities for meaningful communication in a debilitated CNS, while at the same time decreasing proliferative[14] and cytotoxic[15] activities of T lymphocytes. These are precisely the directions in which one would wish to move if one were to attempt to reverse some of the effects observed in AD, ALS and MS, providing an opportunity of restoring normal functional balance in the optimal fashion. Such a dual effect is much more likely to be achieved if all of the desired properties were embodied in one substance than if two or more substances are administered separately albeit simultaneously.

14/ See, Chandy, K. G., deCoursey, T. E., Cahalan, M. D., McLaughlin, C. and Gupta, S., *Journal of Experimental Medicine*, 160, 369-385 (1984).

15/ See, Fukushima, Y., Hagiwara, S. and Henkart, M., *Journal of Physiology*, 351, 645-656 (1984).

Many substances (over 300) were tested for capacity to inhibit K+ transport and acetylcholinesterase. Substances were chosen for testing originally on the basis of known ability to inhibit one or the other of the above processes or because of structural relationships of substances with such properties. Only those substances were selected for further study that inhibited K+ transport in submillimolar concentrations ($10^{-3}$M or less) and inhibited acetylcholinesterase in micromolar ($10^6$M) or lower concentrations. Only five substances met the above criteria. These were the three antimalarials, amodiaquin, quinacrine, and chloroquin; 9-aminoacridine and tetrahydroaminoacridine. Relevant data are reported in Table I:

TABLE I
EFFICACIES OF SUBSTANCES CAPABLE OF BOTH INHIBITION OF POTASSIUM (K+) TRANSPORT AND OF ACETYLCHOLINESTERASE ACTIVITY
Concentrations Producing 50% Inhibition ($IC_{50}$ Values)

| Substances Tested | K+ Transport | | | Acetylcholinesterase Activity | | |
|---|---|---|---|---|---|---|
| | $IC_{50}$ umoles/liter ($10^{-6}$M) | Relative Potency | Rank Order | $IC_{50}$ nmoles/liter ($10^{-9}$M) | Relative Potency | Rank Order |
| Amodiaquin | 40 | 1. | 1 | 4 | 1. | 1 |
| 9-aminoacridine | 70 | 0.57 | 2 | 45 | 0.089 | 2 |
| Quinacrine | 90 | 0.44 | 3 | 4000 | 0.001 | 4(5) |
| Chloroquine | 600 | 0.067 | 4 | 4000 | 0.001 | 5(4) |
| Tetrahydroaminoacridine | 700 | 0.057 | 5 | 45 | 0.089 | 3 |

To obtain the data set forth in Table I, K+-transport was measured using $P_3$ membrane fractions prepared from whole brains of Swiss mice. The tissue was homogenized in 10 vol. of ice-cold 0.25M sucrose and centrifuged at 1050 g for 10 minutes in a Beckman 30 rotor. The resulting supernatant was centrifuged at 17,000 g for 15 minutes, and the supernatant from the latter was centrifuged at 70,000 g for 1 hour to pellet the $P_3$ fraction. The $P_3$ pellet was washed by resuspension in 50 mM Tris-citrate (pH 7.3). After 10 minutes on ice, the suspension was centrifuged at 70,000 g for 10 minutes. This washing procedure was repeated twice using distilled water for the resuspension. The final $P_3$ from 2 grams of whole brain was resuspended in 1.0 ml of 0.32M sucrose containing 0.01M dithiothreitol (DTT). Aliquots of this suspension (6-9 mg protein/ml) could be stored frozen in liquid nitrogen for four weeks with no loss of binding capacity. Prior to the assay, the pellet was thawed by agitating the tube containing it in 39° C. water, then homogenized with double the volume of 0.32M sucrose containing 0.01M DTT. The suspension (2-3 mg protein/ml) was stabilized on ice for 1 hour prior to use. Uptake of $^{86}$Rb (radioactive) was used to assess the K+-transport of the $P_3$ articles. Many published experiments have shown the $^{86}$Rb, with a half-life 36 times longer than $^{42}$K, is a suitable tracer for K. Rb permeates neuronal K channels as well as does K itself.

Uptake studies were carried out routinely in duplicate or triplicate at 0° C. by incubating aliquots of the $P_3$ suspension on ice at pH 7 in a final concentration of $10^{-6}$M RbCl (radioactive), $10^{-3}$M triethanolamine, 0.32M sucrose, 0.01M (DTT) and various concentrations of the test substances. The experiments were terminated after incubation for 5 seconds by rapid filtration through 0.65 μm pore size Millipore filter discs which had been presoaked in distilled water. After filtration of the samples, the filters were washed rapidly three times with $10^{-3}$M triethanolamine containing 0.1M RbCl (non-radioactive) and counted in ACS liquid scintillation cocktail (Amersham). In calculating the results, the uptake found in the presence of 0.1M non-radioactive RbCl was subtracted from that found in the presence of various concentrations of the test substances in the presence of $10^{-6}$M $^{86}$RbCl alone. Uptake was proportional to the amount of $P_3$ protein between 0.1 and 3 mg/ml of incubation mixture. Between 0.2 and 0.5 mg/ml usually were employed. The results were normalized by calculating them as percentages of the uptake observed with $10^{-6}$M $^{86}$RbCl alone.

Cholinesterase activity reported in Table I was measured by a standard procedure. The enzyme employed was prepared from the electric organ of the electric eel. It is known to have the same properties as the enzyme of mammalian nervous tissue. Acetylthiocholine was used as substrate.

The reaction measured is:

Acetylthiocholine

Acetic Acid    Thiocholine

The product, thiocholine, is measured colorimetrically (see Ellman, G. L., *Archives of Biochemistry and Biophysics*, 82, 70-77 (1959)). Inhibitory potency of substances was determined by measuring enzyme activity in the absence and presence of varying concentrations of the test substances.

As Table I shows, amodiaquin is the most effective cholinesterase inhibitor of this group of substances, 9-aminoacridine and tetrahydroaminoacridine possessing less than one-tenth of its inhibitory potency, and chloroquine and quinacrine less than one-thousandth. Amodiaquin also ranked first with regard to K+ transport inhibition, 9-aminoacridine and quinacrine being approximately one-half and chloroquine and tetrahydroaminoacridine approximately one-twentieth as active. Tetrahydroaminoacridine, selected in previous work for testing solely on the basis of its acetylcholinesterase inhibitory potency, has shown ameliorative effects in AD.[16] From the results presented in Table I, it is seen that the latter substance also inhibits K+ transport, albeit considerably less potently than 9-aminoacridine and amodiaquin.

16/ See, Summers, W. K., Kaufman, K. R., Altman, F., Jr. and Fischer, J. M., *Clinical Toxicology*, 16, 269-281 (1980); Summers, W. K., Viesselman, J. O., Marsh, G. M. and Candelora, K., *Biological Psychiatry*, 16, 145-153 (1981); and Summers, W. K., Majovski, L. V., Marsh, G. M., Tachiki, K. and Kling, A. N., *New England Journal of Medicine*, 315, 1241-1245 (1986).

The method of administration is not per se a novel feature of this invention. Hence, amodiaquin may be administered in any manner deemed appropriate by the physician. More specifically, amodiaquin may be administered orally, parenterally or in such other manner as may be or may become known to a person skilled in the art, including oral, programmed release formulations. For example, amodiaquin dihydrochloride tablets, sold under the trade name "Camoquin" by Parke-Davis, may be administered orally. A loading dose of 300 to 500 mg/base body weight is appropriate. Further oral doses of 200 to 400 mg/base body weight may be given at, e.g., 6, 24 and 48 hours.

Amodiaquin dihydrochloride may be dissolved in distilled water at a cocentration from about 10 to about 50 mg/ml, preferably from about 25 to 35 mg/ml, and dispensed in glass vials for intravenous administration. A loading dose of 10 mg base/kg body weight dissolved in 250 ml of normal saline in glass bottles may be infused over a time period of about two to about four hours. Further doses of about 2 to 6, preferably about 5 mg base/kg at four hour infusions, may be given at appropriate time intervals, e.g., 24, 48 and 72 hours. Caution should be taken to protect the amodiaquin dihydrochloride from light. The invention, however, is not limited to any particular dosage or method or means of administration.

The structural formula for amodiaquin is as follows:

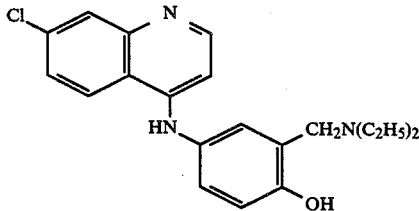

I

Variants and metabolites of amodiaquin having the following generic structural formula are also included within the scope of the invention:

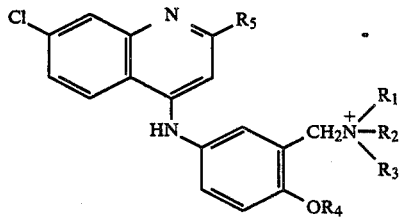

II in which $R_1$, $R_2$ and $R_3$ are each selected from the group consisting of lower alkyls having from 1 to about 5 carbon atoms such as ethyl, methyl, propyl, isopropyl, butyl, isobutyl and the like;

$R_4$ is selected from the group consisting of hydrogen, ether radicals containing from 1 to about 5 carbon atom alkyl groups and ester radicals containing from 1 to about 5 carbon atom alkyl groups; and $R_5$ is selected from the group consisting of hydrogen and hydroxyl.

More specifically, this invention includes therapeutic use of compounds corresponding to generic structural formula II in which $R_1$, $R_2$, $R_3$ and $R_4$ are groups selected from the following Table II and in which $R_5$ is hydrogen or hydroxyl.

TABLE II

| $R_1$ | $R_2$ | $R_3$ | $R_4$ |
|---|---|---|---|
| —CH₃ | —CH₃ | —CH₃ | H, —CH₃, —CH₂CH₃, |
| —CH₃ | —CH₃ | —CH₂CH₃ | —HC(CH₃)₂, —C(O)—CH₃, |
| —CH₃ | —CH₂CH₃ | —CH₂CH₃ | —C(O)—CH₂CH₃, —C(O)—CH(CH₃)₂ |
| —CH₂CH₃ | —CH₂CH₃ | —CH₂CH₃ | |

The invention also includes therapeutic use of compounds corresponding to generic structural formula III:

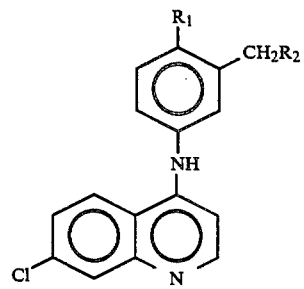

III in which $R_1$ and $R_2$ are selected from the radicals set forth in the following tabulation:

| | $R_1$ | $R_2$ |
|---|---|---|
| 1 | OH | N(piperazine)NCON(C₂H₅)₂ |
| 2 | OCH₃ | N(piperazine)NCON(C₂H₅)₂ |
| 3 | OH | N(piperazine)NCH₃ |
| 4 | H | N(C₂H₅)₂ |
| 5 | OH | NH(C₂H₅) |
| 6 | OCH₃ | N(C₂H₅)₂ |
| 7 | OH | H |

The variants and metabolites of amodiaquin useful in this invention are appropriately administered in the same manner as described above with respect to amodiaquin.

In the preferred practice of the invention, intravenous fluids, intramuscular antipyretics and antiemetics may be given as required. Also in the preferred practice of the invention, no other drugs are administered during the treatment. Blood pressure and pulse rate may appropriately be measured before, during and after the infusion of amodiaquin, a variant or metabolite thereof, and subsequently every three to five hours.

I claim:

1. A method for the treatment of a degenerative disease of the central nervous system of a human which comprises administering to a human affected with such disease a therapeutically effective amount of a compound selected from the group consisting of amodiaquin and a therapeutically effective salt thereof.

2. The method of claim 1 in which the degenerative disease is selected from the group consisting of senile dementia of the Alzheimer's type, multiple sclerosis and amyotrophic lateral sclerosis.

3. The method of claim 2 wherein the compound administered is amodiaquin dihydrochloride.

4. The method of claim 2 in which the degenerative disease is senile dementia of the Alzheimer's type.

5. The method of claim 2 in which the degenerative disease is multiple sclerosis.

6. The method of claim 2 in which the degenerative disease is amyotrophic lateral sclerosis.

7. A method for the treatment of a degenerative disease of the central nervous system of a human which comprises administering to a human affected with such disease a therapeutically effective amount of a compound having the following structural formula:

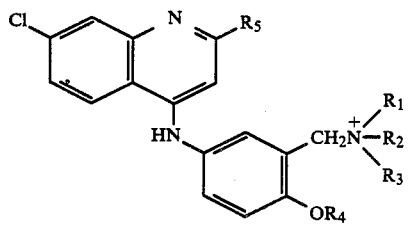

in which
  $R_1$, $R_2$ and $R_3$ are each selected from the group consisting of lower alkyl having from 1 to about 5 carbon atoms such as ethyl, methyl, propyl, isopropyl, butyl, and isobutyl;
  $R_4$ is selected from the group consisting of hydrogen, ether radicals containing from 1 to about 5 carbon atom alkyl group and ester radicals containing from 1 to about 5 carbon atom alkyl groups; and
  $R_5$ is selected from the group consisting of hydrogen and hydroxyl and therapeutically effective salts thereof.

8. The method of claim 7 in which the compound is desethylamodiaquine.

9. The method of claim 7 in which the compound is bisdesethylamodiaquine.

10. The method of claim 7 in which the compound is 2-hydroxydesethylamodiaquine.

* * * * *

UNITED STATES PATENT AND TRADEMARK OFFICE
CERTIFICATE OF CORRECTION

PATENT NO. : 4,806,537

DATED : February 21, 1989

INVENTOR(S) : Eugene Roberts

It is certified that error appears in the above-identified patent and that said Letters Patent is hereby corrected as shown below:

Column 1, after line 9, insert:

--This invention was made with government support under Grant Nos. NS18858, NS18895, and RR01462 awarded by the National Institutes of Health. The government has certain rights in the invention.--

Signed and Sealed this

Ninth Day of February, 1993

Attest:

STEPHEN G. KUNIN

Attesting Officer

Acting Commissioner of Patents and Trademarks